(12) United States Patent
Janbroers et al.

(10) Patent No.: US 8,980,782 B2
(45) Date of Patent: Mar. 17, 2015

(54) BULK SULFIDIC MIXED METAL CATALYST AND METHODS FOR ITS MANUFACTURE AND USE IN CONVERTING SYNGAS TO ALCOHOL

(75) Inventors: Stephan Janbroers, Diemen (NL); Bob Gerardus Oogjen, Almere (NL); Frans Lodewijk Plantenga, Hoevelaken (NL); Harmannus Willem Homan Free, Hoevelaken (NL); Sona Eijsbouts-Spickova, Nieuwkuijk (NL); Edgar Evert Steenwinkel, Santpoort-Zuid (NL); Edwin Nuberg, Zaandam (NL)

(73) Assignee: Albemarle Europe SPRL (BE)

( * ) Notice: Subject to any disclaimer, the term of this patent is extended or adjusted under 35 U.S.C. 154(b) by 689 days.

(21) Appl. No.: 13/203,845

(22) PCT Filed: Mar. 5, 2010

(86) PCT No.: PCT/EP2010/052822
§ 371 (c)(1),
(2), (4) Date: Aug. 30, 2011

(87) PCT Pub. No.: WO2010/100256
PCT Pub. Date: Sep. 10, 2010

(65) Prior Publication Data
US 2011/0319505 A1    Dec. 29, 2011

Related U.S. Application Data

(60) Provisional application No. 61/158,072, filed on Mar. 6, 2009.

(51) Int. Cl.
| | | |
|---|---|---|
| *B01J 27/051* | (2006.01) | |
| *B01J 23/887* | (2006.01) | |
| *B01J 37/00* | (2006.01) | |
| *B01J 37/20* | (2006.01) | |
| *C07C 29/151* | (2006.01) | |

(52) U.S. Cl.
CPC .......... *B01J 27/0515* (2013.01); *B01J 23/8872* (2013.01); *B01J 37/0009* (2013.01); *B01J 37/20* (2013.01); *C07C 29/1518* (2013.01)

USPC .......................................... 502/220; 518/714

(58) Field of Classification Search
CPC ................................. C07C 1/043; B01J 37/20
USPC .......................................... 518/714; 502/220
See application file for complete search history.

(56) References Cited

U.S. PATENT DOCUMENTS

| 4,752,622 | A | 6/1988 | Stevens |
|---|---|---|---|
| 4,831,060 | A | 5/1989 | Stevens |
| 4,882,360 | A | 11/1989 | Stevens |
| 6,294,498 | B1 | 9/2001 | Darcissac |
| 2005/0194291 | A1 | 9/2005 | Brun |
| 2006/0054537 | A1 | 3/2006 | Cholley |
| 2008/0020926 | A1* | 1/2008 | Guillaume et al. ........... 502/314 |
| 2008/0132407 | A1 | 6/2008 | Bai |
| 2009/0018371 | A1 | 1/2009 | Klepper |

FOREIGN PATENT DOCUMENTS

| EP | 0180719 | 5/1986 |
|---|---|---|
| GB | 2065491 | 7/1981 |
| WO | 2006/123158 | 11/2006 |
| WO | 2007/048594 | 5/2007 |
| WO | 2008/045550 | 4/2008 |
| WO | 2008/048364 | 4/2008 |

OTHER PUBLICATIONS

Catal. Lett. (2008) 121:151-157.

* cited by examiner

*Primary Examiner* — Sudhakar Katakam
(74) *Attorney, Agent, or Firm* — Nathan C. Dunn; James A. Jubinsky; Marcy M. Hoefling

(57) ABSTRACT

A process for sulfiding a cobalt-molybdenum bulk catalyst precursor to form a bulk sulfided alcohol synthesis catalyst. The process steps include contacting an oxidic bulk cobalt-molybdenum catalyst precursor with an amount of a sulfur-containing compound which is in the range of about 1 to about 10 moles of sulfur per mole of metals, at one or more temperatures at or in excess of about 300° C. in a medium which is substantially devoid of added hydrogen, so as to form a sulfided bulk cobalt-molybdenum catalyst product. Also described are processes for forming the catalyst precursor, processes for producing an alcohol using the catalyst product and the catalyst product itself.

8 Claims, No Drawings

BULK SULFIDIC MIXED METAL CATALYST AND METHODS FOR ITS MANUFACTURE AND USE IN CONVERTING SYNGAS TO ALCOHOL

PRIORITY CLAIM

This application is a 371 of PCT/EP10/052822 filed on Mar. 5, 2010, which claims priority to Provisional Patent Application No. 611158,072 filed Mar. 6, 2009, the disclosure of which is herein incorporated by reference in its entirety.

FIELD OF THE INVENTION

This invention relates to catalysts for the production of alcohols from synthesis gas, to precursors of such catalysts and to methods of their production and use.

BACKGROUND

Bulk cobalt-molybdenum-sulfide based catalysts are very suitable for the production of alcohols, including mixed alcohols, from synthesis ($CO+H_2$) gas. Synthesis gas can be produced conventionally from almost any carbonaceous material, meaning that bulk cobalt-molybdenum-sulfide based catalysts can facilitate more generally the conversion of carbonaceous material to useful alcohols such as, e.g., ethanol. Most catalyst synthesis routes are based on reactions using ammonium tetrathiomolybdate (($NH_4)_2MoS_4$) as a raw material and a sulfur source in the presence of hydrogen. Due to the air-sensitivity of the catalysts obtained, subsequent process steps like shaping and calcination need to be carried out under inert conditions. On a commercial scale, this poses a real challenge. Prior catalysts in this area also presented environmental concerns because of the starting materials employed.

A need thus persists for improved alcohol synthesis catalysts and improved processes for their production and use.

SUMMARY OF THE INVENTION

This invention provides a new process for conveniently forming a substantially nitrogen-free, oxidic cobalt-molybdenum catalyst precursor suitable for use in producing an activated catalyst useful in alcohol synthesis from synthesis gas (also referred to herein as "syngas"). Through a sulfidation treatment step in accordance with this invention, it is possible to transform the aforesaid mixed metal (cobalt-molybdenum) oxidic precursor into the same active phases as were obtained via previously known sulfidic precipitation routes, all without relying upon the environmentally unfriendly "ammonium thio" precursors such as, for example, ammonium tetrathiomolybdate. The invention also advantageously provides a catalyst precursor which is not sensitive towards oxygen until it has been sulfided. Other routes to prior catalysts useful for alcohol synthesis from syngas required that the catalyst be kept inert from the start of the preparation. In effect, this means the production route of this invention is less complicated and more cost effective. This invention also enables the advantageous recycling of the catalyst precursor mother liquor, because the precursor production process is carried out in the absence of environmentally undesirable starting materials containing counter-ions that accumulate in the mother liquor. For several reasons, the preferred process of the invention meets the highest standard of environmentally friendly and economically optimal catalyst production. Apart from the fact that the metal compounds do not contain nitrogen atoms, also the reaction does not require addition of ammonia to the reaction mixture, as in for example U.S. Pat. No. 4,752,622, so the process is entirely free of nitrogen atoms. There is no accumulation of alien ions like ammonium and/or nitrate in the catalyst precursor mother liquor on repeated recycling, there is no strict need for washing the obtained oxidic particles, there is less environmental burden because of reduced heavy transition metals waste. Because the starting materials remain at least partly solid during the entire reaction, the amount of metals dissolved in the mother liquor is small and hence losses are smaller.

Thus, in one embodiment, the invention provides a process for sulfiding a cobalt-molybdenum bulk catalyst precursor to form a bulk sulfided alcohol synthesis catalyst, the process comprising contacting an oxidic bulk cobalt-molybdenum catalyst precursor with an amount of a sulfur-containing compound which is in the range of about 1 to about 10 moles of sulfur per mole of metals, at one or more temperatures at or in excess of about 300° C. in a medium which is substantially devoid of added hydrogen, so as to form a sulfided bulk cobalt-molybdenum catalyst product.

In some embodiments of the invention, the cobalt-molybdenum bulk catalyst precursor is formed by a precursor formation process comprising combining cobalt(hydroxy)carbonate or cobalt carbonate with molybdenum oxide or molybdic acid in an aqueous medium to form the catalyst precursor comprising cobalt and molybdenum.

Another embodiment of the invention is a process comprising
  forming an oxidic bulk cobalt-molybdenum catalyst precursor by combining cobalt(hydroxy)carbonate or cobalt carbonate with molybdenum oxide or molybdic acid in an aqueous medium to form the catalyst precursor in a form which is substantially free of nitrogen atoms and comprises cobalt and molybdenum; and
  shaping the catalyst precursor so formed.
This process may further comprise
  sulfiding the catalyst precursor under conditions substantially devoid of added hydrogen to form a sulfided bulk catalyst;
  impregnating the sulfided bulk catalyst with a promoter to form an impregnated catalyst product; and
  drying the impregnated catalyst product in an inert atmosphere.

Yet another embodiment of the invention is a process comprising contacting synthesis gas with a catalyst formed in accordance with the teachings set forth herein, the process being carried out under alcohol synthesis reaction conditions so as to form an alcohol.

Still another embodiment of the invention is a bulk catalyst useful in alcohol synthesis from syngas, the catalyst comprising a cobalt component, a molybdenum component, oxygen and sulfur, the catalyst being substantially free of nitrogen atoms.

These and other embodiments, features and advantages of this invention will be still further apparent from the ensuing description, drawings, and appended claims.

FURTHER DETAILED DESCRIPTION OF THE INVENTION

It should now be appreciated that the present invention enables the production of a substantially nitrogen-free oxidic bulk catalyst precursor, easily activated through sulfidation for use in the synthesis of one or more alcohols from syngas. The following will present a detailed description of illustrative embodiments of the invention, including precursor preparation, sulfidation of the precursor, the use of the prepared sulfided catalyst to produce one or more alcohols from syngas and illustrative examples.

For the avoidance of doubt, percentages provided throughout this disclosure are weight percentages unless otherwise indicated.

Precursor Preparation

The cobalt-molybdenum bulk catalyst precursor of this invention is formed by combining into a mixture (a) cobalt (hydroxy) carbonate or cobalt carbonate with (b) molybdenum oxide or molybdic acid, in an aqueous medium. Advantageously, these starting materials are only slightly soluble in water. It should be noted that (a) may more broadly be a Group VIII component (e.g., comprising Ni or Co as the metal) and that (b) may more broadly be a Group VIB component (e.g., comprising Mo or W as the metal).

At least one Group VIII non-noble metal component and at least one Group VIB metal components are applied in the process of the invention. Suitable Group VIB metals include chromium, molybdenum, tungsten, or mixtures thereof, with molybdenum being most preferred. Suitable Group VIII non-noble metals include iron, cobalt, nickel, or mixtures thereof, preferably cobalt and/or nickel.

Group VIII non-noble metal components comprise oxalates, carbonates, hydroxy-carbonates, hydroxides, oxides or mixtures thereof, with hydroxy-carbonates and carbonates being most preferred. Generally, the molar ratio between the hydroxy groups and the carbonate groups in the hydroxy-carbonate lies in the range of 0-4, preferably 0-2, more preferably 0-1 and most preferably 0.1-0.8. In view of obtaining a highly active catalyst it is further preferred that nickel carbonate or hydroxy carbonate having a surface area of at least 150 m$^2$/g, or a cobalt carbonate or hydroxy carbonate having a surface area of at least 50 m$^2$/g.

Suitable molybdenum compounds comprise molybdenum di-and trioxide, molybdic acids (e. g. $H_2MoO_4$), or mixtures thereof, with molybdic acids and molybdenum di-and trioxide being preferred.

The median particle diameter of the metal components preferably is in the range of at least 0.5 μm, more preferably at least 1 μm, most preferably at least 2, but preferably not more than 50 μm, more preferably not more than 100 μm. Generally, the smaller the particle size of the metal components, the higher their reactivity. Therefore, metal components with particle sizes below the preferred lower limits are in principle a preferred embodiment of the present invention. However, for health, safety, and environmental reasons, the handling of such small particles requires special precautions.

In one embodiment of the invention, the amount of (a) relative to the amount of (b) is sufficient to provide a cobalt to molybdenum atomic ratio in the range of about 0.3 to about 3. The amount of water employed can vary widely, but will typically be at least sufficient form an extrudable paste. In one embodiment, the cobalt source and the molybdenum source are brought together in the aqueous medium and maintained in admixture with one another for a period of time (the "reaction time") which can vary depending upon the environmental conditions such as temperature and pressure. The temperature of the mixture is preferably maintained in the range of about 25° C. to about 95° C. during the reaction time. The desired mixed metal oxide can also be obtained when the reaction between the Group VIII and Group VIB components takes place under hydrothermal conditions. The term "hydrothermal conditions" is meant to imply reaction conditions wherein the reaction temperature is above the boiling temperature of the water present. With boiling temperature is meant the boiling temperature at atmospheric pressure. Typically such conditions give rise to a pressure above atmospheric pressure and then the reaction is preferably performed in an autoclave, preferably under autogenic pressure, that is without applying additional pressure.

In the preferred embodiment, hydrothermal conditions imply a pressure higher than 1 bar and a temperature higher than 100° C. The reaction is preferably done in an autoclave under autogenic elevated pressure and temperatures between 110° C. and 170° C. From a process economy point of view it is more attractive to use atmospheric reaction conditions. Typically, the reaction temperature under atmospheric conditions is below 100° C.

The reaction time, both under hydrothermal and atmospheric reaction conditions, is chosen sufficiently long to substantially complete the reaction. The reaction times can be very short, e.g. shorter than 1 hour with highly reactive reactants. Clearly, longer reaction times, perhaps as long as 24 hours, may be required for raw materials with low reactivity. The reaction time can in some circumstances vary inversely with temperature.

Without being bound to theory, it is believed that in this time, the mixed-metal oxide (e.g., of cobalt and molybdenum) is formed and only $CO_2$ evolves.

Upon completion of the reaction time, if necessary, the solid can be separated from the liquid, e.g., via filtration. Typically no washing is required. Conveniently, any mother liquor filtrate may be recycled to make use of mixture components remaining therein. After filtration of the resulting mixture, the precursor filter cake can be shaped. The precursor typically will be shaped prior to sulfidation. Preferably, the bulk precursor particles either as such or comprising any additional materials (described below) are subjected to one or more of the following process steps of (i) compositing with a material selected from the group of binder materials, (ii) spray-drying, (flash) drying, milling, kneading, slurry-mixing, dry or wet mixing, or combinations thereof, (iii) shaping, (iv) drying and/or thermally treating, and (v) sulphiding.

If so desired, additional Mo can be added to the mixed metal oxide precursor during or after its preparation, in order to adjust the Co to Mo atomic ratio, e.g., to be below 1 in one embodiment and to be about 0.5 in another embodiment. In another embodiment, $MoO_3$ and/or molybdic acid is added to the slurry of the mixed metal oxide precursor before solid-liquid separation. In another preferred embodiment, $MoO_3$ and/or molybdic acid is added to the precursor filter cake in the kneader.

If so desired, binder materials can be added during the preparation of the bulk catalyst precursor particles or to the particles after their preparation. The catalyst precursor particles generally are embedded in the binder material, which functions as a glue to hold the particles together. Preferably, the particles are homogeneously distributed within the binder. The presence of the binder generally leads to an increased mechanical strength of the final catalyst composition. Binder material according to this invention means a binder and/or a precursor thereof. If a precursor is added in the form of a solution, care must be taken that the binder is converted to the solid state during the process of the invention. This can be done by adjusting the pH conditions in such a way that precipitation of the binder occurs. Suitable conditions for the precipitation of the binder are known to the skilled person and need no further explanation. If the amount of liquid of the resulting catalyst composition is too high, optionally a solid-liquid separation can be carried out.

Additionally, further materials such as basic promoters, additional transition metals, rare earth metals, or mixtures thereof can be added during the preparation of the bulk catalyst precursor particles.

The binder materials to be applied may be any materials conventionally applied as binders in alcohol synthesis catalysts or Fischer-Tropsch catalysts. Examples are silica, silica-alumina, alumina, titania, zirconia, cationic clays or anionic clays such as saponite, bentonite, kaolin, sepiolite or hydrotalcite, or mixtures thereof. Preferred binders are silica, silica-alumina, alumina, titania, zirconia, bentonite, attapulgite or mixtures thereof. These binders may be applied as such or after peptization. It is also possible to apply precursors of these binders which during the process of the invention are converted into any of the above-described binders.

If desired, the binder material may be composited with a Group VIB metal-containing compound (e.g., Mo or W) and/or a Group VIII non-noble metal-containing compound (e.g., Co or Ni) and/or basic promoter (described below), prior to being composited with the bulk catalyst precursor composition and/or prior to being added during the preparation thereof. Compositing the binder material with any of these metal-containing compounds may be carried out by impregnation of the binder with these materials. Suitable impregnation techniques are known to the person skilled in the art.

Consequently, by adding a binder material, the activity of the bulk catalyst composition may be reduced. Furthermore, the addition of binder material leads to a considerable increase in the mechanical strength of the final catalyst composition. Therefore, the amount of binder material to be added in the process of the invention generally depends on the desired activity and/or desired mechanical strength of the final catalyst composition.

The binder can be added during the preparation of the bulk catalyst precursor particles (see above), subsequent to the preparation of the bulk catalyst precursor composition but prior to any step (ii) and/or during and/or subsequent to any step (ii) but prior to any shaping step (iii).

Preferably, the binder is added subsequent to the preparation of the bulk catalyst precursor particles and prior to spray-drying or any alternative technique, or, if spray-drying or the alternative techniques are not applied, prior to shaping. Optionally, the bulk catalyst precursor composition prepared as described above can be subjected to a solid-liquid separation before being composited with the binder. After solid-liquid separation, optionally, a washing step can be included. Further, it is possible to thermally treat the bulk catalyst precursor composition after an optional solid-liquid separation and drying step and prior to its being composited with the binder.

Optionally, further materials such as basic promoter compounds (described below), additional transition metal compounds, rare earth metal compounds, or mixtures thereof, may be incorporated into the catalyst precursor composition. Suitable additional transition metals are, e.g., manganese, tantalum, rhodium and palladium. Suitable rare earth metals are, e.g. lanthanum and thorium. These metals can be added at any stage of the process of the present invention prior to the shaping step. Apart from adding these metals during the process of the invention, it is also possible to composite the final catalyst composition therewith. Thus it is possible to impregnate the final catalyst composition with an impregnation solution comprising any of these materials.

The bulk catalyst precursor particles optionally comprising any of the above (further) materials can be subjected to spray-drying, (flash) drying, milling, kneading, slurry-mixing, dry or wet mixing, or combinations thereof, with a combination of wet mixing and kneading or slurry mixing and spray-drying being preferred. These techniques can be applied either before or after any of the above (further) materials are added (if at all), after solid-liquid separation, before or after a thermal treatment, and subsequent to re-wetting.

If so desired, the bulk catalyst precursor optionally comprising any of the above (further) materials may be shaped optionally after step (ii) having been applied. Shaping comprises extrusion, pelletizing, beading and/or spray-drying. It must be noted that if the catalyst composition is to be applied in slurry-type reactors, fluidized beds, moving beds, or expanded beds, generally spray-drying or beading is applied. For fixed bed or ebullating bed applications, generally the catalyst composition is extruded, pelletized and/or beaded. The shape and size of the catalyst can vary and will typically depend upon the intended application of the catalyst. In the latter case, at any stage prior to or during the shaping step, any additives which are conventionally used to facilitate shaping can be added. These additives may comprise aluminium stearate, surfactants, graphite, starch, methyl cellulose, bentonite, attapulgite, polyethylene glycols, polyethylene oxides, or mixtures thereof.

After an optional drying step, preferably above 100° C., the resulting shaped catalyst precursor composition may be thermally treated if desired. A thermal treatment, however, is not essential to the process of the invention. A "thermal treatment" according to the invention refers to a treatment performed at a temperature of, e. g., from 100 -1000° C., preferably from 120 to 600° C., for a time varying from 0.5 to 48 hours in an inert gas such as nitrogen, or in an oxygen-containing gas, such as air or pure oxygen. The thermal treatment can be carried out in the presence of water steam.

In all the above process steps the amount of liquid must be controlled. If, e. g., prior to subjecting the catalyst composition to spray-drying the amount of liquid is too low, addition liquid must be added. If, on the other hand, e. g., prior to extrusion of the catalyst composition the amount of liquid is too high, the amount of liquid must be reduced by, e. g., solid-liquid separation via, e. g., filtration, decantation, or evaporation and, if necessary, the resulting material can be dried and subsequently re-wetted to a certain extent. For all the above process steps, it is within the scope of the skilled person to control the amount of liquid appropriately.

The precursor production can be carried out both as a batch process, semi-continuous process or continuous process.

Sulfiding of Precursor

Sulphidation generally is carried out by contacting the bulk catalyst precursor particles directly after their preparation or after any one of process steps (i)-(iv) described above with a sulphur-containing compound. The sulphidation step can be carried out in the liquid or the gaseous phase. It is preferred that the sulphidation is not carried out prior to any process step by which the obtained metal sulphides revert to their oxides. Such process steps are, e. g., a thermal treatment or spray-drying or any other high-temperature treatment if carried out under an oxygen-containing atmosphere.

The sulfur-containing compound employed to sulfide the oxidic bulk catalyst precursor typically will be elemental sulfur, hydrogen sulfide, dimethyl disulfide, one or more organic polysulfides or a mixture of two or more of the foregoing. Example of suitable organic polysulfides include di-tert-butyl polysulfide, di-tert-dodecyl polysulfide, di-tert-nonyl polysulfide. In one particular embodiment, the sulfur-containing compound is hydrogen sulfide. The amount of sulfur-containing compound employed is sufficient to provide in the range of about 1 to about 10 moles of sulfur per mole of metals (total Co+Mo). From literature such as, e.g., Catal. Lett. (2008) 121:151-157, it is believed that the catalyst performance in part depends on the population of surface —SH and/or $S_2^{2-}$ groups available in the catalyst. The population of —SH and/or $S_2^{2-}$ groups depends on the catalyst sulfur content, i.e. catalysts with higher sulfur content will eventually contain a higher number of —SH and/or $S_2^{2-}$ groups under the reaction conditions. Thus, the sulfur to metals ratio of greater than 1 is preferred. More preferably, the sulfur to metals ratio is greater than 1.2.

The sulfiding step is carried out preferably at a temperature at or in excess of 300° C. In one embodiment, the sulfiding step is carried out at a temperature at or in excess of 350° C.

The medium in which sulfidation is carried out is substantially devoid of added hydrogen. A combination of a inert gas (e.g., nitrogen) and the sulfur-containing compound may be used. The amount of sulfur-containing compound should be selected to maximize sulfidation of the mixed metal oxide in the precursor. When the sulfur-containing compound is $H_2S$ in admixture with inert gas, the amount of $H_2S$ is typically in the range of about 20 to about 100 vol %. In another embodiment, the mixed metal oxide precursor is impregnated with melted elemental sulfur and following that heated to a temperature in excess of 350° C. in inert atmosphere.

After sulfidation, additional elements optionally can be impregnated into the sulfided catalytic substrate to enhance catalyst performance. The impregnation of additional components on the sulfided catalyst and the subsequent drying needs to be carried out in inert atmosphere. Examples of suitable additional elements include promoters such as transition metal compounds (e.g. manganese, tantalum, rhodium, palladium), rare earth metal materials (e.g., lanthanum, thorium) and/or basic promoters. Suitable basic promoters include, for example, K, Li, Na, Rb and Cs, alkaline-earth and rare-earth metals. Non-metallic bases can also serve as effective promoters, in some embodiments.

As noted earlier, these metals can be added at any stage of the process of the invention, including, but not limited to, prior to the shaping step of the precursor or as a final step.

Alcohol Synthesis from Syngas

The syngas conversion to one or more alcohols using catalysts formed in accordance with this invention can be carried out under various known process conditions. All such process conditions may also be referred to herein as "alcohol synthesis reaction conditions." In that regard, examples of suitable alcohol synthesis reaction conditions are taught in U.S. Pat. Nos. 4,752,622 and 4,882,360, and US Patent Appl. No. 20090018371, the disclosures of which are incorporated herein by reference.

The alcohol produced through use of the sulfided catalyst of this invention in a syngas conversion process is preferably an aliphatic alcohol or a mixture of aliphatic alcohols. Suitable non-limiting examples of aliphatic alcohols include methanol, ethanol, 1-propanol, 1-butanol, and the like, including all known isomers.

The following examples are presented for purposes of illustration, and are not intended to impose limitations on the scope of this invention.

EXAMPLE 1

A mixed metal oxide was prepared by mixing 1.06 kg cobalt-hydroxy-carbonate (28 wt % Co), 1.14 kg $MoO_3$ (65.7 wt % Mo), 269 g potassium carbonate (99.5% purity), 375 g of a clay binder in the form of attapulgite (LOI=20.5%), a needle-like clay mineral composed of magnesium-aluminum silicate having a lateral dimension above 1 micrometer, and 500 ml demineralized water using a mixer. The mixture that was obtained had an LOI of 40.1 wt % and was extruded in a 3 mm quadrulobe shape. Subsequently the sample was dried at 120° C. overnight.

EXAMPLE 2

50 Grams of a sample obtained from Example 1 was sulfided using a mixture of $H_2S$ (60 vol %) and $N_2$ (40 vol %) while heating with 5° C. per minute ramp up to 350° C., maintaining at this temperature for 120 minutes. To avoid oxidation, the sample was stored under nitrogen gas. The total amount of sulfur dosed, expressed as mole sulfur per mole metals, was 6.0. The sulfur to metals atomic ratio of the sample was found to be: 2.3. The catalyst obtained was used to carry out alcohol synthesis from syngas using the following procedure:

4.2 Grams of a crushed sample, with a particle size in between 0.4 and 0.6 mm, was loaded in a sealable stainless steel reactor with an internal diameter of 16 mm. The temperature of the catalyst was monitored using a thermowell (3 mm diameter) inside the catalyst bed (which was within the isothermal zone of the oven).

All handling was done in glove-box to prevent oxidation of the catalyst. The reactor was then pressurized to 95 bar using nitrogen and heated up to 150° C. with a mixture of 50.7% $H_2$, 31.9% CO and 17.4% N2. The sample was then heated with a ramp of 2° C./minute up to 310° C. After a stabilization period of 20-28 hours, by which all products were kept in the gas phase, gas samples were analyzed using GC. The results are shown in the Table below.

EXAMPLE 3

A mixed metal oxide was prepared by mixing 1.691 kg cobalt-hydroxy-carbonate (44.6 wt % Co), 0.921 kg $MoO_3$ (65.7 wt % Mo), 352 g potassium carbonate (99.5% purity), 491 g of attapulgite (LOI=20.0%), a needle-like clay mineral composed of magnesium-aluminum silicate having a lateral dimension above 1 micrometer, and 1700 ml demineralized water using a mixer. The mixture that was obtained had an LOI of 49.6 wt % and was extruded in a 3 mm quadrulobe shape. Subsequently the sample was dried at 120° C. overnight. The sample obtained was sulfided using a mixture of $H_2S$ (60 vol %) and $N_2$ (40 vol %) while heating with 5° C. per minute ramp up to 350° C., maintaining at this temperature for 180 minutes. To avoid oxidation, the sample was stored under nitrogen gas. The total amount of sulfur dosed, expressed as mole sulfur per mole metals, was 6.0. The sulfur to metals atomic ratio of the sample was found to be: 1.5. The sample obtained was used to carry out alcohol synthesis from syngas using the procedure as described in Example 2. The results are shown in the Table below. The results of Example 3, when compared to Example 2, show that when a Co:Mo ratio of 2.0 is used, a satisfactory catalyst can be obtained, but a catalyst made with a lower Co:Mo ratio is superior.

EXAMPLE 4

100 Grams of a sample obtained from Example 1 was sulfided using a mixture of $H_2S$ (60 vol %) and $N_2$ (40 vol %) while heating with 5° C. per minute ramp up to 350° C., maintaining at this temperature for 240 minutes. To avoid oxidation, the sample was stored under nitrogen gas. The total amount of sulfur dosed, expressed as mole sulfur per mole metals, was 10.0. The sulfur to metals atomic ratio of the sample was found to be: 1.7. The sample obtained was used to carry out alcohol synthesis from syngas using the procedure as described in Example 2. The results are shown in the Table below. The results of Example 4, when compared to Example 2, show that when the total amount of sulfur dosed is 10.0 moles of sulfur per moles of metals, a satisfactory catalyst can be obtained, but a catalyst made with a lower dosing level is superior. Without being bound to any theory, the inventors hereof theorize that the exothermicity of the reaction can play a role. In other words, higher sulfur levels lead to higher catalyst surface temperatures that negatively influence the final catalyst performance.

EXAMPLE 5

100 Grams of a sample obtained from Example 1 was sulfided using a mixture of $H_2S$ (60 vol %) and $N_2$ (40 vol %) while heating with 5° C. per minute ramp up to 300° C., maintaining at this temperature for 180 minutes. To avoid oxidation, the sample was stored under nitrogen gas. The total amount of sulfur dosed, expressed as mole sulfur per mole metals, was 6.0. The sulfur to metals atomic ratio of the sample was found to be: 1.7. The sample obtained was used to carry out alcohol synthesis from syngas using the procedure as described in Example 2. The results are shown in the Table below. The results of Example 5, when compared to Example 2, show that a sulfidation temperature of 300° C. leads to similar results compared to a sulfidation temperature of 350° C.

EXAMPLE 6

100 Grams of a sample obtained from Example 1 was sulfided using a mixture of $H_2S$ (60 vol %) and $N_2$ (40 vol %) while heating with 5° C. per minute ramp up to 400° C., maintaining at this temperature for 220 minutes. To avoid oxidation, the sample was stored under nitrogen gas. The total amount of sulfur dosed, expressed as mole sulfur per mole metals, was 5.2. The sulfur to metals atomic ratio of the sample was found to be: 2.3. The sample obtained was used to carry out alcohol synthesis from syngas using the procedure as described in Example 2. The results are shown in the Table below. The results of Example 5, when compared to Example 2, it shows that a sulfidation temperature of 400° C. leads to similar results compared to a sulfidation temperature of 350° C.

EXAMPLE 7

77 kilo of demineralized water was dosed into a steel 120 liter tank and subsequently heated to 60° C. An amount of 9.71 kg cobalt-hydroxy-carbonate (45.5 wt % Co) was added. While stirring maintaining a vortex, 10.82 kg of $MoO_3$ (65.7 wt % Mo), was dosed in 10 minutes. After this step, another 20 kg of demineralized water was dosed. The mixture was heated to the final reaction temperature of 95° C. After 25 hours at the reaction temperature, the mixture was filtered.

EXAMPLE 8

A part of the filter cake from Example 7 was dried overnight at 120° C. 1.5 kg of the dried filtercake (43.4 wt % solids) was added to a mixer together with 797 g dry base $MoO_3$ (65.7 wt % Mo), 16 gram of a hydroxymethylethylcellulose, 519 g of attapulgite (LOI=20.5%), a needle-like clay mineral composed of magnesium-aluminum silicate having a lateral dimension above 1 micrometer, and 460 g potassium carbonate (99.5% purity). The mixture was heated to evaporate the excess water until an extrusion LOI of 36.3 wt % was obtained. The mixture that was obtained was extruded in a 3 mm quadrulobe shape. Subsequently, the sample was dried at 120° C. overnight. The sample obtained was sulfided using a mixture of $H_2S$ (60 vol %) and $N_2$ mixture (40 vol %) while heating with 5° C. per minute ramp up to 450° C., maintaining at this temperature for 120 minutes. To avoid oxidation, the sample was stored under nitrogen gas. The total amount of sulfur dosed, expressed as mole sulfur per mole metals, was 2.7. The sample obtained was used to carry out alcohol synthesis from syngas using the procedure as described Example 2. The results are shown in the Table below.

EXAMPLE 9

4.63 kg of wet base filtercake from Example 7 (containing 32.4 wt % solids) was added to a mixer together with 10 gram of a hydroxymethylethylcellulose, 375 g of attapulgite (LOI=20.0%), a needle-like clay mineral composed of magnesium-aluminum silicate having a lateral dimension above 1 micrometer, and 200 g potassium carbonate (99.5% purity). The mixture was heated to evaporate the excess water until an extrusion LOI of 38.8 wt % was obtained. The mixture that was obtained was extruded in a 3 mm quadrulobe shape. Subsequently, the sample was dried at 120° C. overnight. The sample obtained was sulfided using a mixture of $H_2S$ (60 vol %) and $N_2$ mixture (40 vol %) while heating with 5° C. per minute ramp up to 400° C., maintaining at this temperature for 190 minutes. To avoid oxidation, the sample was stored under nitrogen gas. The total amount of sulfur dosed, expressed as mole sulfur per mole metals, was 6.0. The sample obtained was used to carry out alcohol synthesis from syngas using the procedure as described in Example 2. The results are shown in the Table below. The results of Example 9, when compared to Example 8, show that at a Co:Mo ratio of 1.0, a satisfactory catalyst can be obtained, but a catalyst having a Co:Mo ratio of 1.0 is not as active as a catalyst having a Co:Mo ratio of 0.5. In addition the MeOH/EtOH ratio increases.

EXAMPLE 10

Comparative

A mixed metal oxide was prepared by mixing 1.74 kg Cobalt-hydroxy-carbonate (28 wt % Co), 1.87 kg $MoO_3$ (65.7 wt % Mo), 437 g potassium carbonate (99.5% purity), 616 g of attapulgite (LOI=20.5%), a needle-like clay mineral composed of magnesium-aluminum silicate having a lateral dimension above 1 micrometer, 20.0 g of a hydroxymethylethylcellulose and 900 ml demineralized water using a mixer. The mixture that was obtained had an LOI of 40.5 wt % and was extruded in a 3 mm quadrulope shape. Subsequently the sample was dried at 120° C. overnight. The sample obtained was sulfided using a mixture of $H_2S$ (15 vol %) and $N_2$ (85 vol %) while heating with 5° C. per minute ramp up to 350° C., maintaining at this temperature for 120 minutes. To avoid oxidation, the sample was stored under nitrogen gas. The total amount of sulfur dosed, expressed as mole sulfur per mole metals, was 1.2. The sample obtained was used to carry out alcohol synthesis from syngas using the procedure as described in Example 2. The results show that lowering the amount of sulfur during activation has a negative effect on the activity and total alcohol production. In addition the MeOH/EtOH ratio increases.

EXAMPLE 11

Comparative

100 Grams of a sample obtained from example 1 was sulfided using a mixture of $H_2S$ (7 vol %) $H_2$ (5 vol %) and $N_2$ (88 vol %) while heating with 5° C. per minute ramp up to 350° C., maintaining at this temperature for 190 minutes. To avoid oxidation, the sample was stored under nitrogen gas. The total amount of sulfur dosed, expressed as mole sulfur per mole metals, was 6.0. The sulfur to metals atomic ratio of the sample was found to be: 1.7. The sample obtained was used to carry out alcohol synthesis from syngas using the procedure as described in Example 2. The results show that a sulfidation with hydrogen leads to a lower CO conversion and a lower selectivity towards ethanol.

EXAMPLE 12

4.63 kg of wet base filtercake from Example 7 (containing 32.4 wt % solids) was added to a mixer together with 0.981 kg $MoO_3$ (65.7 wt % Mo), 15 gram of hydroxymethylethylcellulose, 547 g of attapulgite (LOI=20.0%), a needle-like clay mineral composed of magnesium-aluminum silicate having a lateral dimension above 1 micrometer. The mixture was heated to evaporate the excess water until an extrusion LOI of 34.9 wt % was obtained. The mixture that was obtained was extruded in a 3 mm quadrulobe shape. Subsequently, the sample was dried at 120° C. overnight. 100 Grams of the sample obtained was sulfided using a mixture of $H_2S$ (60 vol %) and $N_2$ mixture (40 vol %) while heating with 5° C. per minute ramp up to 450° C., maintaining at this temperature for 190 minutes. To avoid oxidation, the sample was stored under nitrogen gas. The total amount of sulfur dosed, expressed as mole sulfur per mole metals, was 5.3. 50 Grams of the sulfided sample was impregnated via incipient wetness impregnation using a solution of 6.0 g $K_2CO_3$ (99.9% purity) in 30.0 ml of demineralized water under nitrogen. After dosing, the samples were aged for 1 hour after which the sample was dried by heating with a ramp of 5° C./minute up to 190° C. for 1 hour. The final sample was stored under nitrogen. The sample obtained was used to carry out alcohol synthesis from syngas using the procedure as described in Example 2. The results are shown in the table below. Compared to example 8, it shows that potassium post impregnation leads to a similar catalyst performance as potassium introduced by co-extrusion.

| EXAMPLE# | 2 | 3 | 4 | 5 | 6 | 8 | 9 | 10 | 11 | 12 |
|---|---|---|---|---|---|---|---|---|---|---|
| Runtime, Hr Activity | 21.8 | 23.4 | 23.1 | 23.7 | 27.3 | 23.9 | 23.7 | 24.7 | 24.6 | 24.7 |
| CO conversion, % | 25.1 | 13.5 | 15.4 | 26.1 | 27.6 | 14.0 | 11.0 | 14.3 | 18.7 | 13.7 |
| Selectivity | | | | | | | | | | |
| CH4 sel. mole % | 9.7 | 9.2 | 9.3 | 12.3 | 10.0 | 8.4 | 16.0 | 9.8 | 9.8 | 7.2 |
| CO2 sel., mole % | 31.0 | 25.1 | 29.1 | 31.8 | 32.2 | 31.1 | 33.0 | 29.0 | 25.9 | 24.5 |
| MeOH sel, mole % | 25.1 | 35.1 | 31.2 | 23.5 | 22.4 | 27.5 | 31.5 | 31.0 | 35.0 | 33.3 |
| EtOH sel, mole % | 34.2 | 30.6 | 30.4 | 32.4 | 35.4 | 33.0 | 19.5 | 30.2 | 29.3 | 33.5 |
| % MeOH/% EtOH ratio | 1.5 | 2.3 | 2.1 | 1.5 | 1.3 | 1.7 | 3.2 | 2.1 | 2.4 | 2.0 |
| MeOH/EtOH production | | | | | | | | | | |
| g · MeOH/Hr/g · cat | 0.095 | 0.071 | 0.064 | 0.090 | 0.092 | 0.061 | 0.058 | 0.060 | 0.088 | 0.071 |
| g · EtOH/Hr/g · cat | 0.093 | 0.044 | 0.045 | 0.089 | 0.104 | 0.052 | 0.026 | 0.042 | 0.053 | 0.051 |
| Wet chemical analysis | | | | | | | | | | |
| Molar Co:Mo ratio | 0.5 | 2.0 | 0.5 | 0.5 | 0.5 | 0.5 | 1.0 | 0.5 | 0.5 | 0.5 |
| S/metals ratio (mole/mole) | 2.3 | 1.4 | 1.6 | 1.6 | 2.3 | 1.8 | 0.7 | 1.7 | 1.3 | 1.3 |

It is to be understood that the reactants and components referred to by chemical name or formula anywhere in this document, whether referred to in the singular or plural, are identified as they exist prior to coming into contact with another substance referred to by chemical name or chemical type (e.g., another reactant, a solvent, or etc.). It matters not what preliminary chemical changes, transformations and/or reactions, if any, take place in the resulting mixture or solution or reaction medium as such changes, transformations and/or reactions are the natural result of bringing the specified reactants and/or components together under the conditions called for pursuant to this disclosure. Thus the reactants and components are identified as ingredients to be brought together in connection with performing a desired chemical operation or reaction or in forming a mixture to be used in conducting a desired operation or reaction. Also, even though an embodiment may refer to substances, components and/or ingredients in the present tense ("is comprised of", "comprises", "is", etc.), the reference is to the substance, component or ingredient as it existed at the time just before it was first contacted, blended or mixed with one or more other substances, components and/or ingredients in accordance with the present disclosure.

Also, even though the claims may refer to substances in the present tense (e.g., "comprises", "is", etc.), the reference is to the substance as it exists at the time just before it is first contacted, blended or mixed with one or more other substances in accordance with the present disclosure.

Except as may be expressly otherwise indicated, the article "a" or "an" if and as used herein is not intended to limit, and should not be construed as limiting, the description or a claim to a single element to which the article refers. Rather, the article "a" or "an" if and as used herein is intended to cover one or more such elements, unless the text expressly indicates otherwise.

Each and every patent or other publication or published document referred to in any portion of this specification is incorporated in toto into this disclosure by reference, as if fully set forth herein.

This invention is susceptible to considerable variation within the spirit and scope of the appended claims.

That which is claimed is:

1. A process of manufacturing a sulfided bulk cobalt-molybdenum catalyst, comprising the steps of,
(a) forming an oxidic bulk cobalt-molybdenum catalyst precursor by combining cobalt (hydroxy) carbonate or cobalt carbonate with molybdenum oxide or molybdic acid in an aqueous medium to form the catalyst precursor in a form which is free of nitrogen atoms and comprises cobalt and molybdenum, wherein the starting materials remain at least partly solid during the entire reaction;
(b) shaping the catalyst precursor so formed;

(c) contacting the oxidic bulk cobalt-molybdenum catalyst precursor with an amount of a sulfur-containing compound which is in the range of 1 to 10 moles of sulfur per mole of metals, at one or more temperatures at or in excess of 300° C. in a medium which is devoid of added hydrogen, so as to form a sulfided bulk cobalt-molybdenum catalyst product.

2. The process according to claim 1, wherein the sulfiding reaction is conducted in the presence of an inert gas.

3. The process according to claim 1, wherein the aqueous medium further comprises a promoter, selected from alkali metal, manganese or magnesium.

4. The process according to claim 1, wherein the cobalt-molybdenum bulk catalyst precursor formation process is carried out at one or more temperatures either (a) in the range of 25 to 95° C. under ambient pressure or (b) above 95° C. under autogenous pressure.

5. The process according to claim 1, wherein the cobalt to molybdenum atomic ratio is 0.5 or higher, preferably 1 or higher.

6. The process according to claim 1, wherein the precursor formation process further comprises adding a source of additional molybdenum to the aqueous medium in an amount sufficient to provide a cobalt to molybdenum atomic ratio of less than 1, wherein the source of additional molybdenum is preferably selected from the group consisting of molybdenum oxide and molybdic acid.

7. The process according to claim 1, wherein the sulfur-containing compound is selected from the group consisting of hydrogen sulfide, elemental sulfur, dimethyl disulfide, one or more organic polysulfides or a combination of any two or more of the foregoing.

8. The process according to claim 1, wherein the amount of the sulfur-containing compound is sufficient to provide a sulfur to total metals (Co+Mo) molar ratio of 1 or greater.

* * * * *